(12) United States Patent
Brandstätter et al.

(10) Patent No.: US 7,869,575 B2
(45) Date of Patent: Jan. 11, 2011

(54) X-RAY EXAMINATION SYSTEM FOR ANALOG MAMMOGRAPHY

(75) Inventors: Werner Brandstätter, Nürnberg (DE); Wolfgang Holler, Erlangen (DE); Martin Ramsauer, Pyrbaum (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 11/587,075

(22) PCT Filed: Mar. 9, 2005

(86) PCT No.: PCT/EP2005/051063

§ 371 (c)(1),
(2), (4) Date: Oct. 20, 2006

(87) PCT Pub. No.: WO2005/106580

PCT Pub. Date: Nov. 10, 2005

(65) Prior Publication Data

US 2007/0263766 A1    Nov. 15, 2007

(30) Foreign Application Priority Data

Apr. 28, 2004  (DE) .................. 10 2004 020 719

(51) Int. Cl.
*H05G 1/28* (2006.01)
(52) U.S. Cl. ....................... 378/166; 378/165
(58) Field of Classification Search .................. 378/37, 378/162, 165, 166
See application file for complete search history.

(56) References Cited

U.S. PATENT DOCUMENTS

| | | | |
|---|---|---|---|
| 4,860,330 A | 8/1989 | Strömmer et al. | 378/162 |
| 5,195,122 A * | 3/1993 | Fabian | 378/165 |
| 5,311,567 A | 5/1994 | Pellegrino et al. | 378/166 |
| 7,085,346 B1 * | 8/2006 | Virta et al. | 378/37 |
| 2001/0051256 A1 | 12/2001 | Silagy et al. | 428/212 |

FOREIGN PATENT DOCUMENTS

| | | |
|---|---|---|
| DE | 3633289 A1 | 3/1988 |
| DE | 41 40 718 A1 | 6/1992 |

(Continued)

OTHER PUBLICATIONS

IPER dated Jul. 3, 2006 with English translation.

(Continued)

*Primary Examiner*—Jurie Yun
(74) *Attorney, Agent, or Firm*—Brinks, Hofer, Gilson & Lione (57) ABSTRACT

An X-ray examination system for analog mammography is provided. The X-ray examination system for analog mammography includes an X-ray system including an X-ray film and labeling device. The X-ray film is exposed to an X-ray beam of the X-ray system with examination images of a patient. The labeling device includes an exposure beam for exposing the X-ray film with additional patient-specific information. The labeling device is a structural component of the X-ray system and is separate from the X-ray system for exposing the X-ray film. The labeling device is positionable relative to the X-ray film. The labeling device is disposed outside the X-ray beam or in the direction of an exposure of the X-ray film.

21 Claims, 6 Drawing Sheets

FOREIGN PATENT DOCUMENTS

| | | |
|---|---|---|
| DE | 601 05 208 T2 | 9/2005 |
| EP | 0 414 042 A2 | 2/1991 |
| EP | 0 474 552 A1 | 3/1992 |
| JP | 58-130335 | 8/1983 |

OTHER PUBLICATIONS

German Office Action for DE 10 2004 020 719.4-35 dated Dec. 15, 2004 with English translation.
German Office Action dated Feb. 5, 2010 with English translation.

* cited by examiner

X-RAY EXAMINATION SYSTEM FOR ANALOG MAMMOGRAPHY

This patent document claims the benefit of PCT/EP2005/051063 filed on Mar. 9, 2005, which is hereby incorporated by reference. This patent document also claims benefit of DE 10 2004 020 719.4 filed on Apr. 28, 2004, which is hereby incorporated by reference.

BACKGROUND

1. Field

The present embodiments relate to an X-ray examination system for analog mammography.

2. Related Art

German Patent Disclosure DE 41 40 718 A1 discloses an X-ray examination system. In analog mammography, the examination picture is of the object being examined. In addition to the examination picture, different kinds of patient-specific information are applied to an X-ray film. As examples of such information, the orientation of the object being imaged is exposed on the film. The orientation information is in the form of a standardized, adjustable letter abbreviation. The orientation information is exposed by film markers thrust into the beam path. Additional information such as data on the person being examined and settings of the measurement equipment are additionally exposed on the film with the aid of a labeling device.

DE 41 40 718 A1 discloses an X-ray film that is placed in a film cassette. The labeling device is either accommodated, remaining fixed, in the film cassette, or a corresponding light source outside the film cassette is disposed in the X-ray system. The exposure beam of the light source is directed onto the X-ray film via a mirror by a marking window in the film cassette.

U.S. Pat. No. 5,311,567 A discloses a labeling device that is structurally separate from the X-ray system. The film cassette, with the X-ray film located in it, is removed from the X-ray system and inserted into the separate labeling device.

While assuring a precise, unmistakable association of the patient-specific information with the particular X-ray film, secure protection of the labeling device against an undesired influence of the X-ray beam in the examination situation is assured.

In one exemplary embodiment, an X-ray examination system for analog mammography includes an X-ray system including an X-ray film and labeling device. The X-ray film is exposed to an X-ray beam of the X-ray system with examination images of a patient. The labeling device includes an exposure beam for exposing the X-ray film with additional patient-specific information. The labeling device is a structural component of the X-ray system and is separate from the X-ray system for exposing the X-ray film. The labeling device is positionable relative to the X-ray film. The labeling device is disposed outside the X-ray beam or in the direction of an exposure of the X-ray film.

The system for X-ray examination according to at least one embodiment permits secure protection of the labeling device from the X-ray beam. In one embodiment, this is accomplished in a simple way and with little effort, with compulsory mutual association of the X-ray film and the labeling device as a structural part of the X-ray system. Accordingly, in this embodiment, unmistakability of the information to be exposed is assured, by the mutual, variable positionability of the labeling device and X-ray film and by the positionable screen element.

In one embodiment, various cassette formats are used. Only one labeling device that remains operative in the X-ray system is necessary. Commercially available film cassettes can be used. This reduces the cost. In addition, the marking by film markers is eliminated because the information is integrated with the exposure by the labeling device, by way of the orientation of the object being imaged.

In one embodiment with a compact design, an object table is associated with the X-ray system. The object table is provided for holding both the X-ray film and the labeling device.

In one embodiment, the X-ray film is disposed in a film cassette, and the film cassette has a window for the exposure beam of the labeling device. In this embodiment, cost is reduced and commercially available components are used. In another embodiment, a user input unit is disposed in the X-ray system. A touch-sensitive input unit such as a touch panel, is with the labeling device. In another embodiment, a user input unit jointly controls the X-ray system. This embodiment eliminates one additional user input unit and simplifies the handling of the entire system.

DETAILED DESCRIPTION

Figure 1:
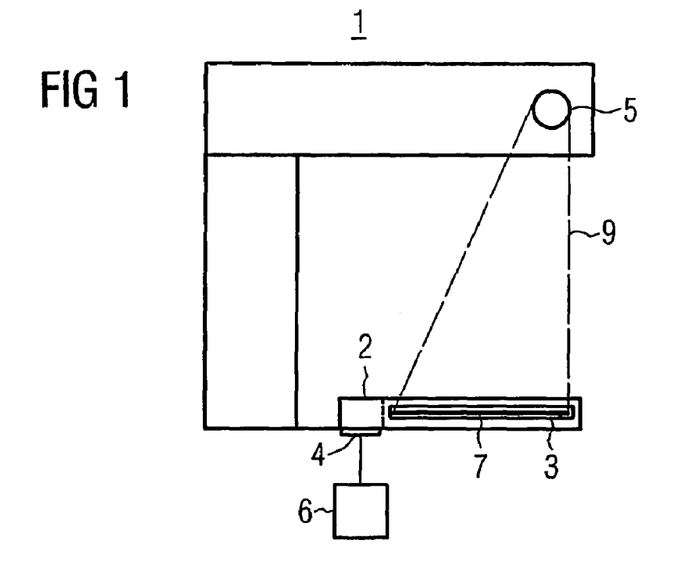
FIG. 1 illustrates a system for analog mammography/X-ray examination with an associated labeling device that is movable in an object table.

In one embodiment, as shown in FIG. 1, an analog X-ray system 1, for example, a mammography X-ray system, includes an X-ray emitter 5 and an object table 2. During examination, the X-ray emitter 5 generates an X-ray beam 9, which creates an image of an object being examined, not explicitly shown, of a patient on an X-ray film 7. The X-ray film 7 is disposed in a film cassette 3. The object table 2 includes the X-ray film 7 and film cassette. A labeling device 4 is integrated, as a structural component, with the X-ray system 1 and is controlled by a user input unit 6. The labeling device 4 exposes whichever X-ray film 7 is put in place with additional patient-specific information. The labeling device 4 is disposed below the X-ray film 7 or film cassette 3 or object table 2 and supports them. In one embodiment, the labeling device 4 is movable into any suitable position.

Figure 2:
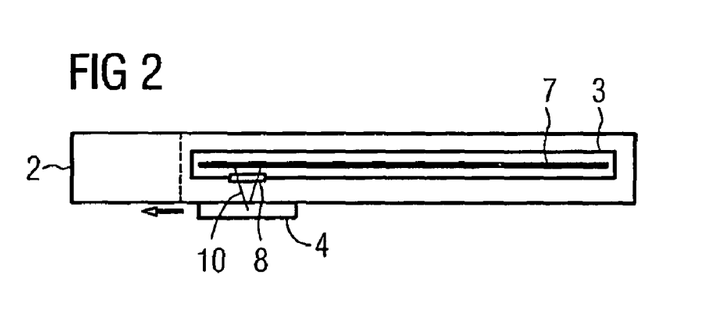
FIG. 2 illustrates an object table with X-ray film and with a labeling device that is moved into the labeling position.

FIG. 2 shows a detail of the object table 2 of FIG. 1 with an associated labeling device 4. The film cassette 3 has a cassette window 8 for the exposure beam of the labeling device 4. During the exposure of the X-ray film 7 with additional patient-specific information, the labeling device 4 is moved in a position underneath the labeling device 8. In this embodiment, the exposure beam 10 strikes the X-ray film 7.

In one embodiment, the X-ray film 7 is fixed, and the labeling device 4 is movable, relative to the X-ray film, into its exposure position. The arrow indicates the direction in which the particular element is movable.

Figure 3:
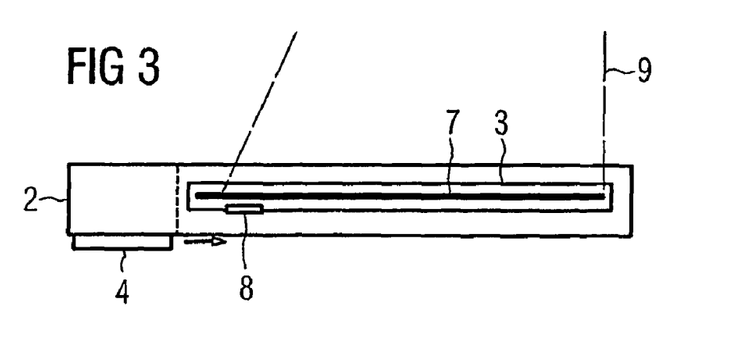
FIG. 3 illustrates an object table with X-ray film and with a labeling device that is moved into the examination position.

In one embodiment, as shown in FIG. 3, the labeling device 4 is positioned outside the X-ray beam 9. In this embodiment, the X-ray beam 9 is prevented from damaging the labeling device 4 and the positioning is done by moving the labeling device 4 relative to the object table 2.

Figure 4:
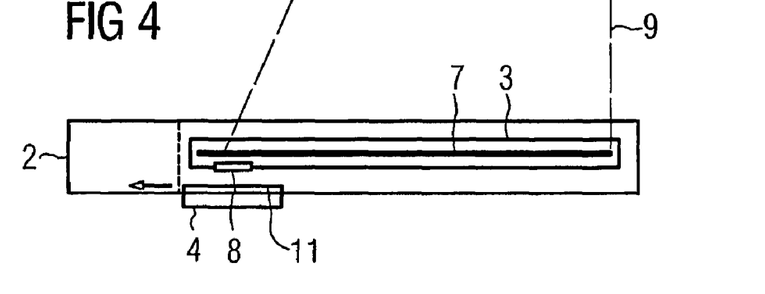
FIG. 4 illustrates a side view of an object table with the X-ray film, the labeling device, and a screen element moved into the examination position.
Figure 5:
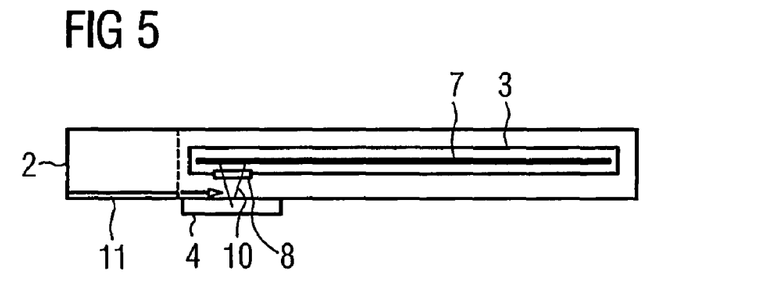
FIG. 5 illustrates a side view of an object table with the X-ray film, the labeling device, and a screen element moved into the labeling position.

In one embodiment, as shown in FIGS. 4 and 5, a screen element 11 shields the labeling device 4 from the X-ray beam 9. A lead plate is provided for the screen element 11. As shown in FIGS. 4 and 5, the labeling device 4 and the X-ray film 7 are fixed, and the screen element 11 is movable relative to the labeling device 4. In one embodiment, as shown in FIG. 4, the screen element 11 is in the examination position. For example, the screen element 11 is disposed between the labeling device 4 and the X-ray beam 9 in such a way that it shields the labeling device 4 against the X-ray beam 9. FIG. 5 illustrates the position of the screen element 11 during the labeling operation. For example, the screen element 11 is positioned adjacent to the labeling device 4. The exposure beam 10 exposes the X-ray film 7 with the additional patient-specific information.

Figure 6:
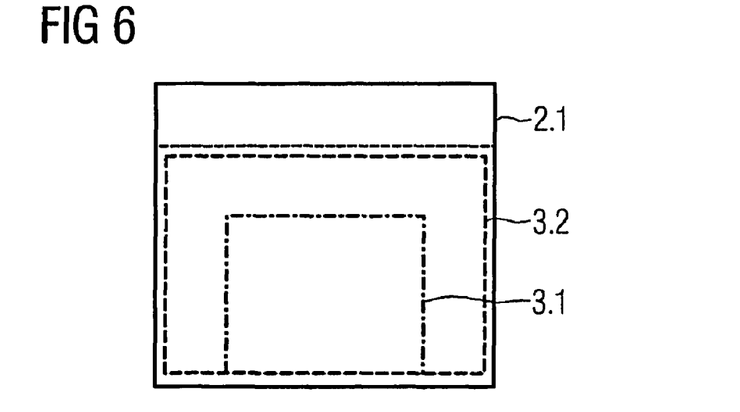
FIG. 6 illustrates a plan view of a dual-format object table.

In one embodiment, as shown FIG. 6, an object table 2.1 has two different formats of X-ray films in respective film cassettes 3.1 and 3.2 of different format. In one embodiment, a large-format X-ray film has a large-format film cassette 3.2. In one exemplary embodiment, the labeling device is disposed in the labeling position as in FIG. 2 and in the examination position as in FIG. 3.

Figure 7:
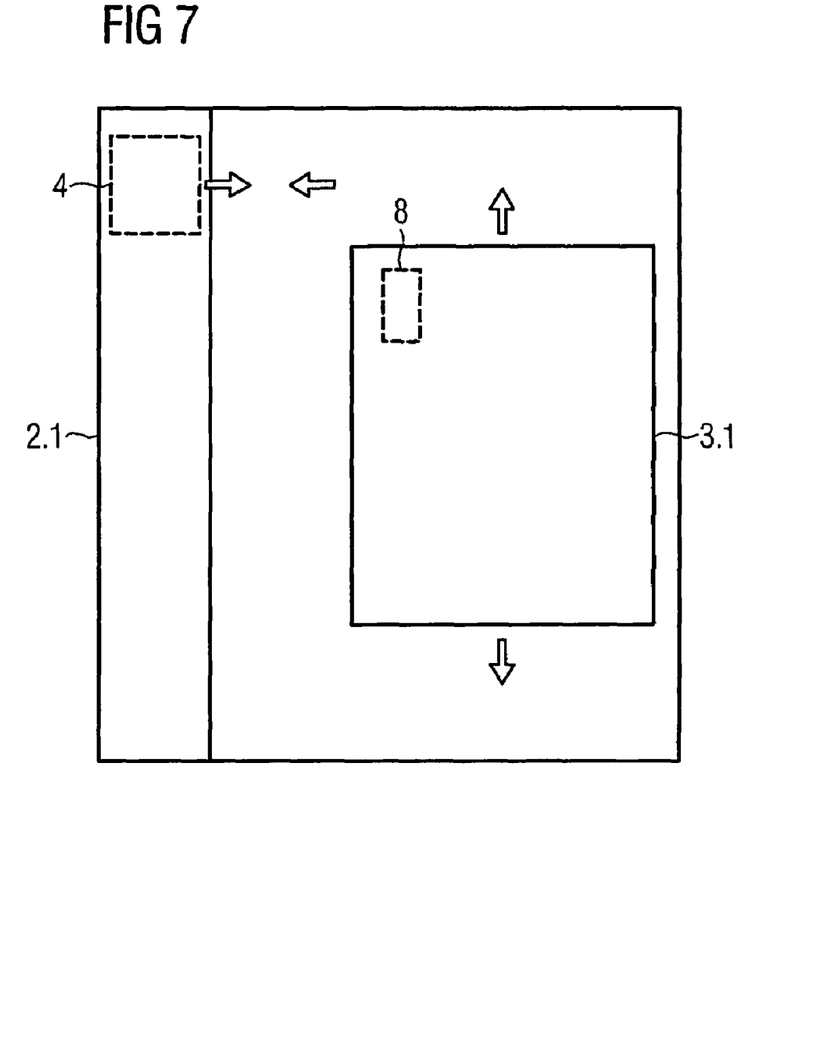
FIG. 7 illustrates a plan view of a dual-format object table with a small-format film cassette moved into the examination position and with a labeling device.
Figure 8:
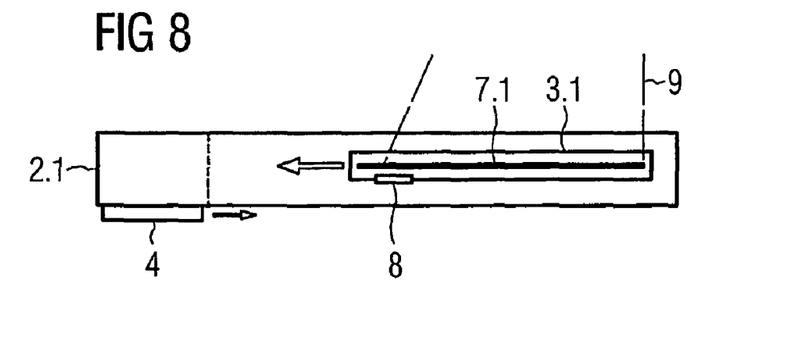
FIG. 8 illustrates a side view of a dual-format object table as in FIG. 7.
Figure 9:
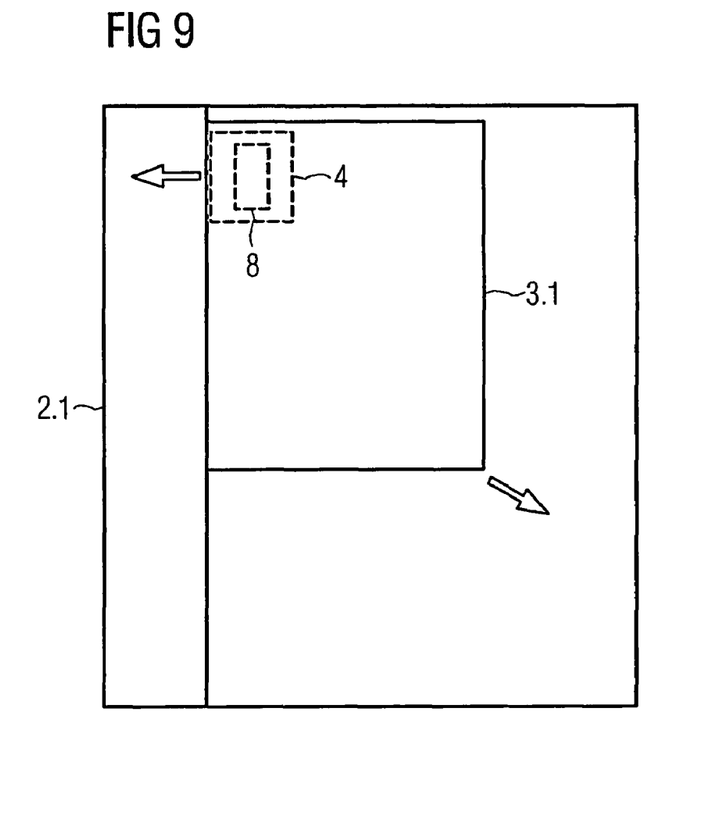
FIG. 9 illustrates a plan view of a dual-format object table with a small-format film cassette and a labeling device that are moved into the labeling position.
Figure 10:
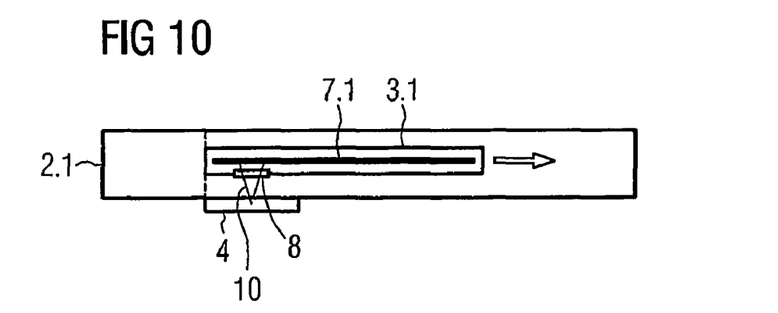
FIG. 10 illustrates a side view of a dual-format object table as in FIG. 9.

FIGS. 8-14 illustrate exemplary embodiments. FIGS. 7, 9, 11, and 13 are in plan view, and FIGS. 8, 10, 12 and 14 are in side view, and show various possible embodiments of the labeling device 4 and a small-format X-ray film 7.1 in a small-format film cassette 3.1 with a window 8. FIGS. 7 through 10 show an exemplary embodiment in which the labeling device 4 and the X-ray film 7 are movable. For example, Fig. and FIG. 8 show exemplary positions of the labeling device 4 and X-ray film 7.1 when moved in the examination situation. In another example, FIG. 9 and FIG. 10 show positions of the labeling device 4 and X-ray film 7.1 during the labeling situation. In one embodiment, the cassette 3.1 is laterally movable into the examination position, as indicated in FIG. 7 by the arrows pointing sideways.

Figure 11:
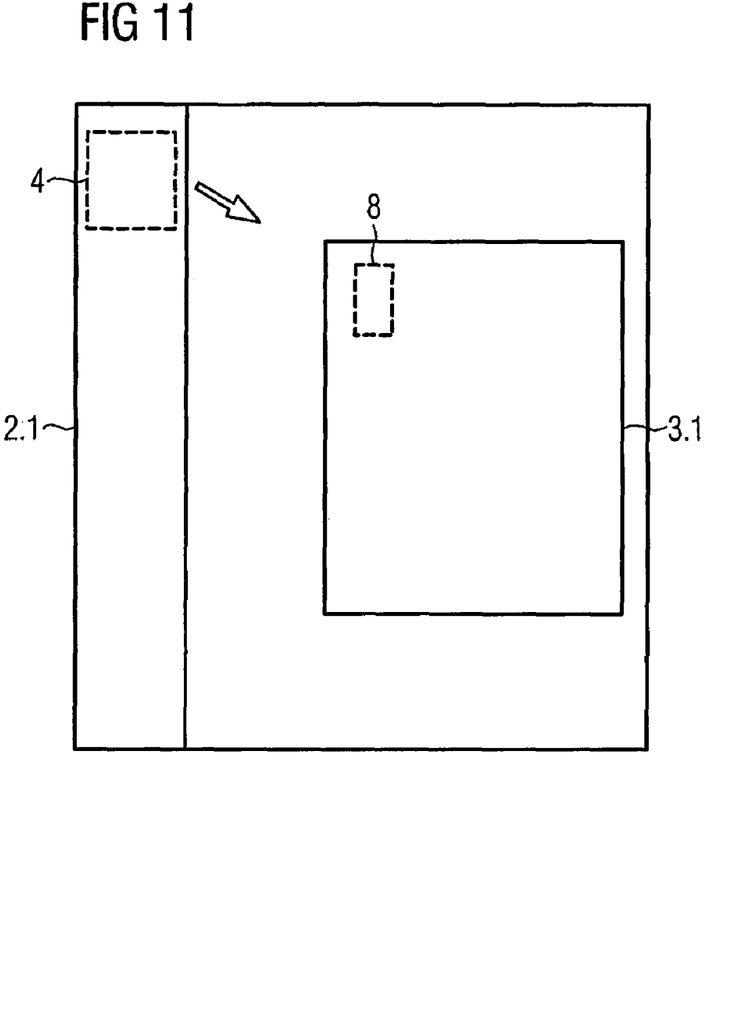
FIG. 11 illustrates a plan view of a dual-format object table with a small-format film cassette and with a labeling device that is moved into the examination position.
Figure 12:
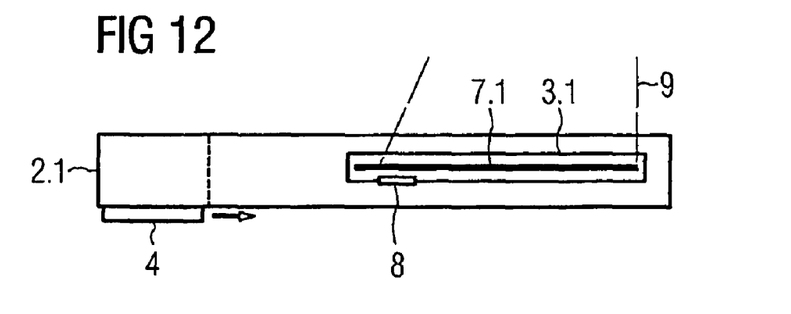
FIG. 12 illustrates a side view of a dual-format object table as in FIG. 11.
Figure 13:
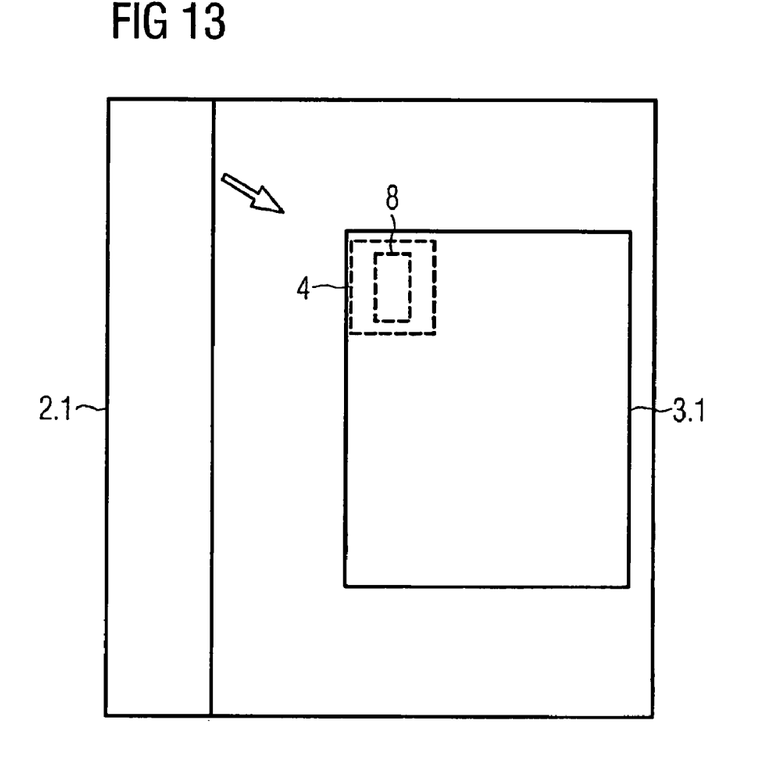
FIG. 13 illustrates a plan view of a dual-format object table with a small-format film cassette and with a labeling device that is moved into the labeling position.
Figure 14:
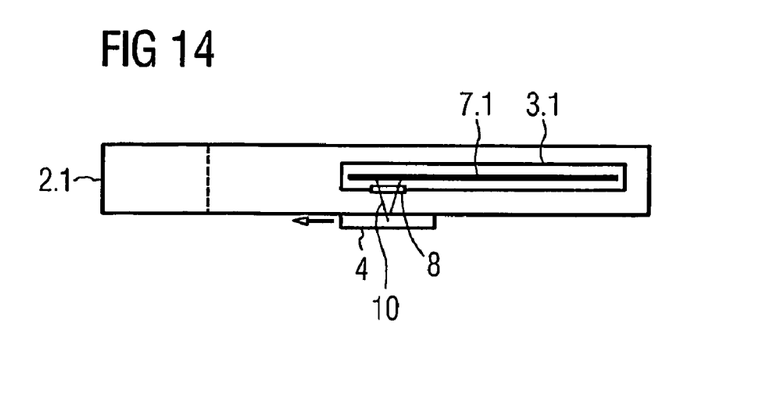
FIG. 14 illustrates a side view of a dual-format object table as in FIG. 13.

FIGS. 11 through 14 show the object table 2.1 with a fixed positioned small-format X-ray film 7.1 and a movable labeling device 4. As shown in FIG. 11 and in FIG. 12, the dual-format object table 2.1 is shown during the examination situation, for example, with the labeling device 4 moved outside the X-ray beam field. As shown in FIG. 13 and FIG. 14, the labeling device is moved to expose the X-ray film 3.1 with additional information by the exposure beam 10, for example, during the labeling situation.

In one embodiment, the labeling device 4 and/or the X-ray film 7 and/or the screen element 11 are movable into their respective positioning, for example, relative to the object table 2. The embodiments are not limited to those shown in the drawings. For example, both the labeling device 4 and the X-ray film 7 and the screen element 11 are movable relative to one another, for example, the elements have mutual movability.

One embodiment is briefly summarized as follows: To simplify labeling an X-ray film 7; 7.1, which can be exposed with examination images of a patient, with additional patient-specific information, in a system for X-ray examination, particularly for analog mammography, a structurally integrated labeling device 4 and an X-ray film 7; 7.1 are positionable relative to one another in such a way that the labeling device 4 is disposed outside the X-ray beam 9 in the examination situation and in the direction of an exposure of the X-ray film 7; 7.1 in the labeling situation. In another embodiment, the labeling device 4, during the making of the X-ray image, has a screen element 11 provided on the side of the X-ray film remote from the X-ray beam. In this embodiment, the labeling device 4 is covered relative to the X-ray beam 9 in the examination situation.

The invention claimed is:

1. An X-ray examination system for analog mammography, comprising:
   an X-ray system including an X-ray film and a labeling device;
   the X-ray film being exposed to an X-ray beam of the X-ray system with examination images of a patient; and
   the labeling device including an exposure beam for exposing the X-ray film with patient-specific information, the labeling device is an integrated, structural component of the X-ray system providing the X-ray beam,
   wherein the labeling device is positionable relative to the X-ray film and is operable to be moved into and out of an area exposed to the X-ray beam, such that labeling device is operable to be positioned out of the area exposed to the X-ray beam when the X-ray film is exposed to the X-ray beam and in the area exposed to the X-ray beam when the X-ray film is not exposed to the X-ray beam.

2. The X-ray examination system as defined by claim 1, having an object table operative with the X-ray system, wherein the object table supports the X-ray film and the labeling device.

3. The X-ray examination system as defined by claim 1, wherein the X-ray film is disposed in a film cassette.

4. The X-ray examination system as defined by claim 3, wherein the film cassette has a window for the exposure beam.

5. The X-ray examination system as defined by claim 1, wherein the X-ray film is fixed, and the labeling device is movable.

6. The X-ray examination system as defined by claim 1, wherein the labeling device and the X-ray film are movable.

7. The X-ray examination system as defined by claim 1, wherein the labeling device and the X-ray film are fixed, and a screen element is movable.

8. The X-ray examination system as defined by claim 1, wherein a user input unit is a touch-sensitive input unit and is disposed in the X-ray system operative with the labeling device.

9. The X-ray examination system as defined by claim 8, wherein the user input unit controls the X-ray system, and is jointly operative with the labeling device.

10. An X-ray examination system for analog mammography, the X-ray examination system comprising:
- an X-ray film that is exposed to an X-ray beam with examination images of a patient;
- a labeling device that uses an exposure beam for exposing the X-ray film with patient-specific information, the labeling device is integrated, as a structural component, with the X-ray system and is in compulsory fashion with the X-ray film, the labeling device is a component separate from X-ray film; and
- a screen element that is disposed on a side of the X-ray film remote from the X-ray beam,
- wherein the screen element is operable to be positioned between the labeling device and the X-ray film when the X-ray film is exposed to an X-ray beam and is operable to be positioned out of an area exposed to the exposure beam when the X-ray film is exposed to the patient-specific information, and
- wherein the screen element shields the labeling device from the X-ray beam when the X-ray film is exposed to an X-ray beam.

11. The X-ray examination system as defined by claim 10, wherein the screen element is a lead plate.

12. The X-ray examination system as defined by claim 10, having an object table operative with the X-ray system, wherein the object table supports the X-ray film and the labeling device.

13. The X-ray examination system as defined by claim 12, wherein the labeling device, the X-ray film, the screen element, or any combination thereof is movable relative to the object table.

14. The X-ray examination system as defined by claim 13, wherein the X-ray film is fixed, and the labeling device is movable.

15. The X-ray examination system as defined by claim 13, wherein the labeling device and the X-ray film are movable.

16. The X-ray examination system as defined by claim 10, wherein the X-ray film is disposed in a film cassette.

17. The X-ray examination system as defined by claim 16, wherein the film cassette has a window for the exposure beam.

18. The X-ray examination system as defined by claim 10, wherein the labeling device and the X-ray film are fixed, and the screen element is movable.

19. The X-ray examination system as defined by claim 10, wherein a user input unit is a touch sensitive input unit and is disposed in the X-ray system operative with the labeling device.

20. The X-ray examination system as defined by claim 19, wherein the user input unit controls the X-ray system, and is jointly operative with the labeling device.

21. An X-ray detection system for analog mammography, comprising:
- an X-ray film;
- an X-ray film cassette operable to support the X-ray film during an examination;
- a labeling device attached to the X-ray film cassette, the labeling device including an exposure beam for exposing the X-ray film with patient-specific information, the labeling device is structured to be moved into and out of an area exposed to an X-ray beam; and
- a screen element that is operable to be positioned between the labeling device and the X-ray film cassette during an X-ray examination and is operable to be positioned out of an area exposed to the exposure beam when the X-ray film is exposed to the patient-specific information, the screen element shielding the labeling device from the X-ray beam during the X-ray examination.

* * * * *